(12) United States Patent
Keller

(10) Patent No.: US 6,743,258 B1
(45) Date of Patent: Jun. 1, 2004

(54) KNEE PROSTHESIS SYSTEM

(75) Inventor: Arnold Keller, Kayhude (DE)

(73) Assignee: Waldemar Link (GmbH & Co.), Hamburg (DE)

( * ) Notice: Subject to any disclaimer, the term of this patent is extended or adjusted under 35 U.S.C. 154(b) by 322 days.

(21) Appl. No.: 09/869,374

(22) PCT Filed: Oct. 27, 2000

(86) PCT No.: PCT/EP00/10585
§ 371 (c)(1),
(2), (4) Date: Jun. 28, 2001

(87) PCT Pub. No.: WO01/34069
PCT Pub. Date: May 17, 2001

(30) Foreign Application Priority Data

Nov. 9, 1999 (EP) .............................. 99122314

(51) Int. Cl.$^7$ .................................. A61F 2/38
(52) U.S. Cl. ................. 623/20.14; 623/20.15; 623/20.31; 606/88
(58) Field of Search ............... 623/20.14, 20.15, 623/20.21, 20.23, 20.31; 606/82, 88, 99

(56) References Cited

U.S. PATENT DOCUMENTS

| 3,949,428 A | | 4/1976 | Cavendish et al. | |
|---|---|---|---|---|
| 5,171,244 A | * | 12/1992 | Caspari et al. | 606/88 |
| 5,234,433 A | * | 8/1993 | Bert et al. | 606/88 |
| 5,520,695 A | * | 5/1996 | Luckman | 606/88 |

FOREIGN PATENT DOCUMENTS

| EP | 0 824 904 A2 | 2/1998 |
|---|---|---|
| FR | 2 589 720 | 5/1987 |
| WO | 79/00739 | 10/1979 |

* cited by examiner

Primary Examiner—Paul Prebilic
(74) Attorney, Agent, or Firm—Morrison & Foerster LLP

(57) ABSTRACT

A knee prosthesis system includes a single-piece tibia plateau with two sliding cavities, a single-piece femur component with two condylar sliding surfaces, the distances between and shapes of which are adapted to the tibial sliding cavities and a pair of unconnected femoral condylar cups, the shapes of the sliding surfaces of which are adapted to the tibial sliding cavities. To be able also to adapt their relative positions, including their distances apart, to the sliding cavities, the system includes a position instrument which ensures this adapted relative position of the codylar cups.

16 Claims, 2 Drawing Sheets

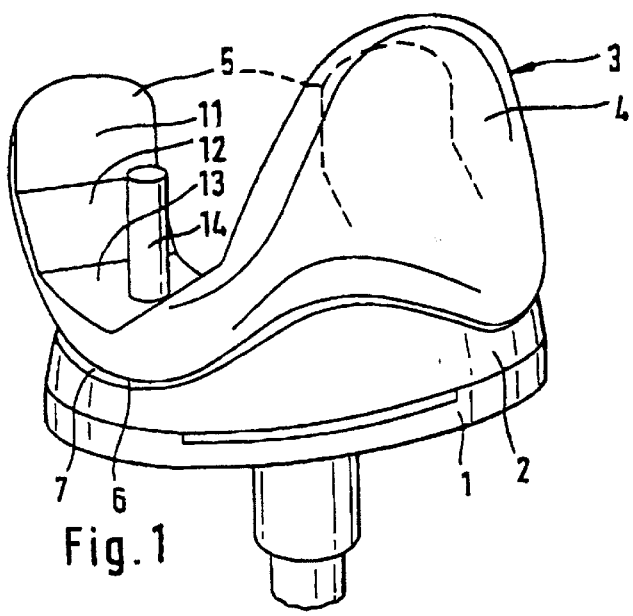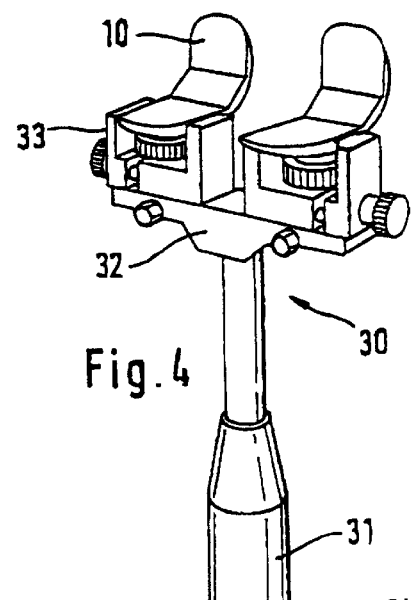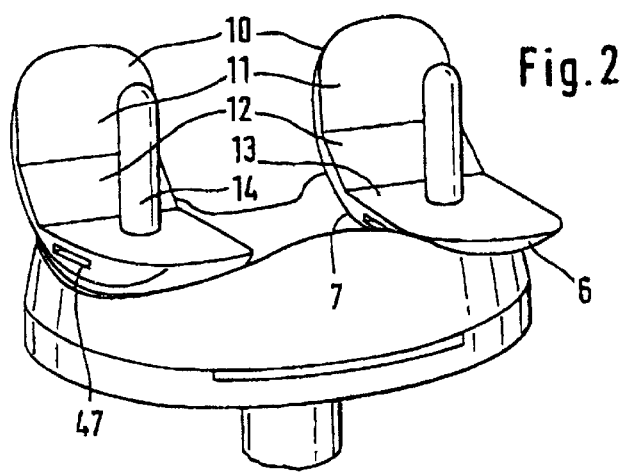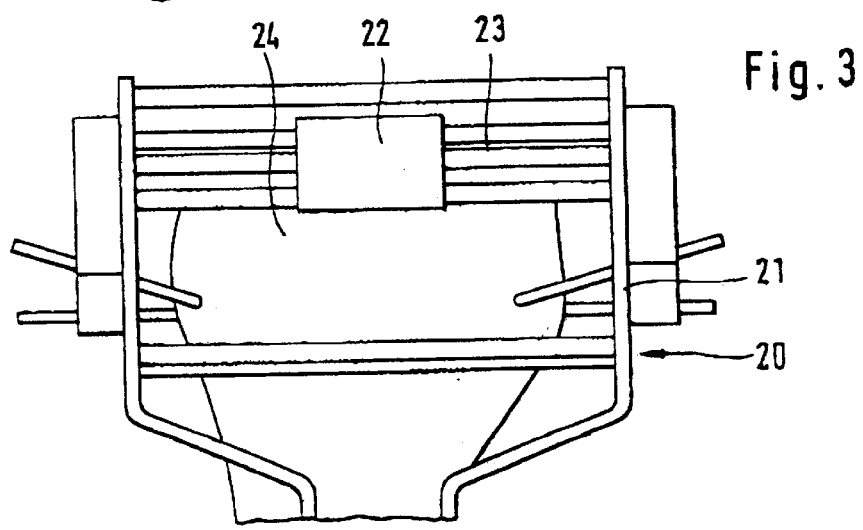

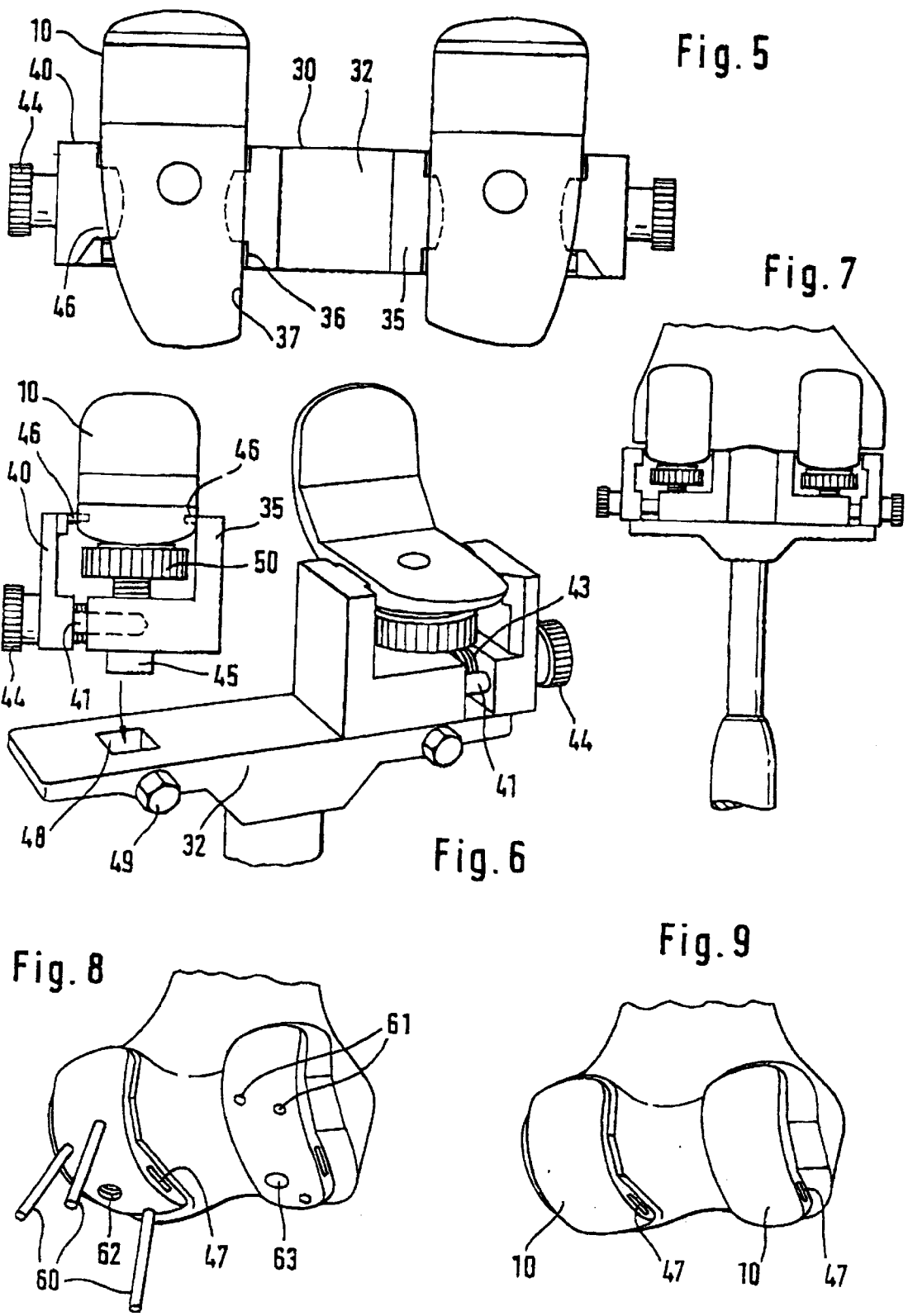

KNEE PROSTHESIS SYSTEM

The human knee joint contains two tibio-femoral pairs of articular surfaces, namely a medial pair and a lateral pair of articular surfaces, which are respectively formed by a femoral condyle and a cup-shaped tibial or meniscal articular surface interacting with it. In knee prostheses, these anatomical conditions are simulated by two femoral, condyle-shaped articular surfaces and two cup-shaped articular surfaces on the tibia side. The lateral distance between the femoral articular surfaces must in this case correspond exactly to the distance between the tibial articular surfaces. To ensure this, the femoral articular surfaces on the one hand and the tibial articular surfaces on the other hand are generally formed in a single piece (U.S. Pat. No. 4,081,866; WO/79/007339, FIG. 36). Although it is also known, WO/79/007339, FIG. 34) to use for the replacement of the femoral articular surfaces femorally unconnected single prostheses which interact with cup-shaped tibial articular surfaces connected in a single piece, this is rejected nowadays because it is not ensured that the distance between and alignment of the femoral sliding surfaces match the tibial part of the prosthesis.

Similarly regarded as outmoded is a prosthesis technique in which unconnected femoral and tibial parts of the prosthesis are implanted by means of one and the same positioning instrument, which ensures the same distance between the sliding surfaces on both sides (U.S. Pat. No. 3,949,428). Furthermore, it is known in those cases in which replacement of the articular surfaces takes place only on one side (femoral or tibial) or where an exact alignment of the interacting articular surfaces faces does not matter, to implant the unconnected parts of the prosthesis by means of a positioning instrument which ensures that they are parallel (EP-A 824 904; W. Link: brochure "Schalen-Kniegelenk-prothesen-System SKI" [cup knee joint prosthesis system SKI]).

To sum up, it can be stated that known modern knee prosthesis systems which provide a femoral articular surface replacement and tibial articular surface replacement as total prostheses and in which the tibial sliding surfaces formed in a cup-shaped manner are designed to fit exactly with the femoral sliding surfaces only ever have femoral sliding surfaces connected in a single piece. One of the reasons why this configuration has established itself is that it offers the possibility of forming a sliding surface for the patella, or a patella replacement, which connects the parts of the femoral sliding surfaces as a patella plate (U.S. Pat. No. 4,081,866). Since prostheses of this type have proved successful, they are often also used when the femoral patella slideway is still well preserved and actually need not be replaced.

The invention requires a knee prosthesis system which comprises a single-piece tibia plateau with two sliding cavities and a single-piece femur component with two condylar sliding surfaces, the distance between and shape of which are adapted to the tibial sliding cavities. It additionally creates an implantation alternative for those cases in which the femoral patella sliding surface is still so well preserved that it need not be replaced, in that it adds to this system, as an alternative to the single-piece femur component, a pair of connected femoral condylar cups, the shape of the sliding surfaces of which is similarly adapted to the tibial sliding cavities like the condylar sliding surfaces of the single-piece femur component. In order that they also assume precisely that position in relation to each other that the condyles of the single-piece component have in relation to each other, the system also includes a positioning instrument for the condylar cups, which gives them a relative position adapted to the tibial sliding cavities.

The invention makes it possible to use one and the same knee prosthesis system for different injuries. If the entire sliding surfaces of the replacement so require, the single-piece condyle component is used. If, on the other hand, the patella sliding surfaces are still in a good condition, only the condylar sliding surfaces are replaced. Moreover, it is possible by a comparatively minor intervention to replace the condylar cups by a single-piece femur component if it should be found over time that the patella sliding surfaces need replacing as well. Finally, an intraoperative change of the initially provided, less radical variant to the more radical variant is also possible.

At the same time, it is not necessary to dispense with complicated shapes of sliding surfaces, as have been developed in the case of single-piece prostheses. This is so because it has so far been customary to design separate prosthesis cups and/or the associated tibia sliding surfaces in such a way that they can tolerate implantation inaccuracies, because their shapes need not be exactly matched to one another. However, it is possible within the scope of the system according to the invention, by the addition of the positioning instrument, similarly to shape the separate prosthesis cups such that they are adapted to the tibial component, like the corresponding condylar parts of the single-piece femur component, because a sufficiently precise implantation is ensured. The shape of and distance between the sliding surfaces of the condylar cups can therefore coincide with the shape of and distance between the condylar sliding surfaces of the single-piece femur component.

Furthermore, it is expedient if the condylar resection surfaces which are required for the positioning of the condylar cups coincide with the corresponding resection surfaces of the single-piece femur component. This not only has the advantage that the same sawing gage can be used. Rather, it also makes it easier to change over from one variant of the femoral prosthesis to the other.

Since the single-piece femur component extends over the entire width of the femur condyles, the associated sawing cuts are to be made not only in the region of the condyles but also in the intermediate region. The latter is not required when using condylar cups. It may even be harmful if—depending on the position of the resection cuts—part of the femoral sliding surface region of the knee cap could also be affected. It is therefore provided according to the invention that the sawing gage which is used for both variants of femur prostheses has in the intercondylar region a blocking lug which allows the operating surgeon to spare the intercondylar region or even restrict the condylar cuts to the mutually facing sides in exact accordance with the intended position of the edges of the condylar cups.

The restrictions of the condylar cups may be chosen to take any desired form. However, it is expedient if they face mutually parallel, straight side surfaces. This is because their exact alignment with the positioning instrument is then easier, if the latter has matching parallel connecting surfaces.

The prosthesis system according to the invention normally includes a number of size stages with different distances between the condylar cups. The invention correspondingly provides that the mutual distance between the parallel connecting surfaces of the positioning instrument can be set differently in stages. Their adjustability is expediently based on the use of exchangeable parts, which are in each case assigned only to one stage because this reduces the risk of erroneously setting the distance between the condylar cups. A preferred embodiment of the invention provides that the connecting surfaces of the positioning instrument—whether they are parallel or not—are formed by in each case a fixed jaw of individual clamps which are respectively assigned to a condylar cup and for which, according to a further feature, different mounts assigned to the individual size stages are used.

Further advantageous features of the invention emerge from the following description of an exemplary embodiment with reference to the drawings, in which:

FIG. 1 shows an overall view of the prosthesis with a single-piece femoral component, FIG. 2 shows the same with a two-piece femoral component, FIG. 3 shows the sawing gage, FIG. 4 shows the positioning instrument, FIG. 5 shows the positioning instrument with condylar cups attached to it, in plan view, FIG. 6 shows a perspective partial view of the positioning instrument, FIG. 7 shows the positioning instrument with condylar cups while the latter are being placed onto the bone, FIG. 8 shows the trial cups fixed on the bone after removal of the positioning instrument and FIG. 9 shows the prosthesis cups in the attached state.

According to FIG. 1, the prosthesis comprises a tibia plate 1, to be anchored to the upper end of the shin bone, a polyethylene tibia plateau 2 held rotatably on the latter and a single-piece femur component 3, which has a patella plate 4 for forming a patella sliding surface and condylar parts 5 for forming condylar sliding surfaces 6. For receiving the condylar sliding surfaces 6, the tibia plateau 2 contains correspondingly shaped cavities 7. On account of the single-piece design of the tibia plateau 2 of the femur component 3, it is ensured that the sliding surfaces of the two components shaped to correspond to one another interact in an exactly matching manner.

FIG. 2 shows that configurational variant in which the single-piece femur component 3 is replaced by a pair of condylar cups 10, which are shaped in exactly the same way as the condylar parts 5 of the single-piece femur component 3; they have been, as it were, cut off from the single-piece component. Their sliding surfaces 6 correspond precisely to the sliding surfaces 6 of the single-piece component and interact in the same way with the sliding cavities 7 of the tibia plateau, provided that their relative positioning corresponds exactly to that of the condylar parts 5 of the single-piece component. The parts of the prosthesis are available in several size stages.

The anchorage surfaces of the femur components 3 and 10 facing the bone are composed in a coinciding polygonal form from planes 11, 12, 13, which correspond to coinciding resection surfaces on the bone. Anchorage pins 14 located at a coinciding point are also provided. The resection and anchorage surfaces of the component 3 which are assigned to the patella plate 4 are of course not provided on the condylar cups 10.

Used for the resection of the femur condyles is the sawing gage 20 represented in FIG. 3, which is known per se (WO 98/53747) and therefore does not require a detailed description. It contains several pairs of guide rods 22 between side walls 21 for fixing the planes in which a bone saw for producing the resection cuts is guided. If the single-piece component 3 is to be used, the cuts extend over the entire width of the osseous pair of condyles. If only condylar cups 10 are to be attached, the sawing gage 20 is provided with a blocking insert 23, which protects the intercondylar region. Its side surfaces are parallel and in line with those lines which are intended to be followed by the inner side edges of the condylar cups in the intended position. The blocking insert 23 protects the intercondylar region from undesired cuts. A number of blocking inserts are available, in each case matching a size stage of the prosthesis.

The positioning instrument 30 represented in FIG. 4 serves for the positionally correct attachment of the condylar cups 10 to the femur bone. It comprises a grip 31, a mounting plate 32 and two clamps 33 for receiving the condylar cups 10. To be able to fit the parts together more conveniently, a base 34 is provided, which contains a vertical bore matching the diameter of the grip part 31 and which holds the instrument while the condylar cups are being put into place and being clamped in the position represented.

As FIG. 5 reveals, the clamps 33 have inner clamping jaws 35, which form parallel connecting surfaces 36 for the inside edges 37 of the condylar cups. The interaction of the surfaces 36 with the edges 37 provides a precisely parallel alignment of the cups 10. It goes without saying that the same could also be achieved if these surfaces were not of a straight shape; however, the straight shape facilitates production and visual checking that the cup is fitted correctly. Moreover, it is appropriate for the anatomical conditions.

On their outer sides, the clamps 33 are formed by a movable jaw 40, which is guided parallel to the fixed, inner jaws 35. In the example represented, the guidance takes place by guiding rods 41, which interact with corresponding bores of the clamping base 42, which is rigidly connected to the inner, fixed jaw 35. The presetting takes place by means of a threaded spindle 43 and a knob 44 connected to it on the outside. The jaws 35, 40 are provided with mutually facing projections 46. The edges of the condylar cups contain recesses 47, which match these projections. The projections and recesses are of an elongate configuration and, as a result, make the condylar cups assume a predetermined direction in the positioning instrument.

From the underside of the clamping base 42 there protrudes a pin 45, which is formed to fit respectively in a receiving opening 48 in the mounting plate 32. The pin 45 and the receiving opening 48 are formed in such a way that they do not turn in relation to each other, in the example represented thanks to a square cross section. The pins can be secured in the receiving openings by means of screws 49. The two receiving openings 48 in the mounting plate 32 run parallel to each other.

For each size stage belonging to the prosthesis system, a separate mounting plate 32 is provided. The mounting plate of different size stages differ by their width in the LM direction and by the distance between their receiving openings 48. The associated clamps 33 may coincide. Instead of this, it would also be possible to use different clamps and one and the same mounting plate, the arrangement of the pins 47 at the clamps ensuring the desired distance of the same from one another. Finally, it is also conceivable to use just one mounting plate which has a greater number of receiving openings 48, which allow the mounting of clamps at different distances apart.

Each clamp 33 contains between the jaws 35, 40 the widely formed head 50 of an adjusting screw guided in the clamping base 42. The surface of the head 50 is covered with a compliant material, for example polyethylene. Once a condylar cup 10 has been clamped between the jaws 35, 40, the adjusting screw 50 is screwed against the sliding surface facing it and supports the latter. This is therefore also referred to in the claims as the sliding surface support. It serves the purpose of permitting a force transmission from the positioning instrument to the condylar cups in the direction of placement when the cups are placed onto the bone, without the forces having to be transmitted by the projections 46. Furthermore, the sliding surface supports 50 contribute to the correct positioning of the condylar cups in the positioning instrument if the movable clamping jaw 40 has play with respect to the other clamping jaw 35 or the projections 46 have play with respect to the depressions 47 receiving them.

If a pair of condylar cups 10 is to be placed onto the resected bone, they are initially seized in the way explained by the positioning instrument. This is then placed, as shown in FIG. 7, with the condylar cups onto the bone. As soon as the condylar cups are fixed, firstly the mounting plate 32 with the grip part 31 of the positioning instrument is removed, by loosening the screws 49 and pulling the mounting plate 32 off the clamps 33 and their pins 45. This is possible because the two clamps 33 are connected to the holding plate 32 in the same loosening direction of their pins 45. Subsequently, the clamps 33 can be loosened from the cups, by screwing back the movable jaw 40, possibly after the sliding surface support 50 has first been loosened. If the condylar cups are the final parts of the prosthesis, the positioning implement is removed once they have been sufficiently anchored to the bone with cement or in a cement-free manner. If they are trial implants, they are first fastened to the bone by means of fixing pins 60, for which bores 61 are provided in the condylar cups. These bores lie outside the region covered by the clamps, so that the pins 60 can be inserted as long as the prosthesis cups are still fixed by the positioning instrument. At that point where the implants have an anchorage pin 14, the trial implants have a bore 62 of a corresponding size. If a bore for receiving the pins has not already been made in the bone in advance, this can be performed by the bore 62 of the trial implants at the correct point. After that, a fixing bolt 63 is pressed into the bore 62 and the bone bore lying thereunder, the said fixing bolt then being able to hold the trial implants instead of the removed fixing pins 60 and its head disappearing in the bore 62. The positioning of the implant and the articular function can then be checked with the aid of the trial implants. Once this has been removed, the prosthesis cups to be finally used are attached in the same way.

What is claimed is:

1. A knee prosthesis system, comprising in combination a single-piece tibia plateau having two tibial sliding cavities, a single-piece femur component having two condylar sliding surfaces, the distance between and shape of which are adapted to the tibial sliding cavities and a pair of unconnected femoral condylar cups each having a condylar sliding surface the shape of which is adapted to the tibial sliding cavities, a positioning instrument which gives the condylar cups of the pair of unconnected pair of condylar cups predetermined positions relative to each other and to the tibial sliding cavities of the single-piece tibial plateau and a sawing gage having cutting planes in predetermined positions relative to the single-piece femur component and the pair of unconnected condylar cups.

2. The knee prosthesis system according to claim 1, wherein the shape of and distance between the sliding surfaces of the unconnected condylar cups coincide with the shape of and distance between the condylar sliding surfaces of the single-piece femur component.

3. The knee prosthesis system according to claim 2, wherein the positions of condylar resection surfaces of the single-piece femur component and of the unconnected condylar cups coincide.

4. The knee prosthesis system according to claim 3, wherein the sawing gage has coinciding cutting planes both for the single-piece femur component and for the unconnected condylar cups.

5. The knee prosthesis system according to claim 4, wherein the sawing gage has a removable blocking insert in an intercondylar region between the unconnected condylar cups.

6. The knee prosthesis system according to claim 4, wherein the unconnected condylar cups face parallel side surfaces and the positioning instrument has matching parallel connecting surfaces.

7. The knee prosthesis system according to claim 6, wherein the distance between the parallel connecting surfaces is adjustable in stages corresponding to different distances between the unconnected condylar cups belonging to different size stages.

8. The knee prosthesis system according to claim 7, wherein the adjustability of the distances between the parallel connecting surfaces is provided by the use of adjustable parts.

9. The knee prosthesis system according to claim 6, wherein the connecting surfaces are formed by a fixed jaw comprising separate clamps which are assigned to each of the unconnected condylar cups.

10. The knee prosthesis system according to claim 9, further comprising mounts of different widths for receiving the clamps.

11. The knee prosthesis system according to claim 10, wherein the clamps can be removed from the mount in the same loosening direction.

12. The knee prosthesis system according to claim 9 or 10, wherein the unconnected condylar cups and the clamps comprise interacting elevations and depressions for positioning the unconnected condylar cups and the clamps relative to each other.

13. The knee prosthesis system according to claim 9 or 10, wherein the jaws of the clamps act on the unconnected condylar cups in an LM direction and comprise an adjustable sliding surface support.

14. The knee prosthesis system according to claim 1, further comprising trial condylar cups which have bores for fixing pins grasped by the positioning instrument.

15. The knee prosthesis system according to claim 14, wherein the unconnected condylar cups comprise at least one anchorage pin and the trial condylar cups contain at point of this pin a bore for a fixing bolt with a head which can be recessed in the bore.

16. The knee prosthesis system according to claim 9 or 10, wherein the adjustability of the distance between the parallel connecting surfaces is provided by the use of adjustable parts.

* * * * *